US00PP23027P2

(12) United States Plant Patent
Egger

(10) Patent No.: US PP23,027 P2
(45) Date of Patent: Sep. 11, 2012

(54) ***ROSCOEA* PLANT NAMED 'SPICE ISLAND'**

(50) Latin Name: *Roscoea purpurea*
Varietal Denomination: Spice Island

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/068,997

(22) Filed: May 24, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(74) *Attorney, Agent, or Firm* — Klarquist Sparkman, LLP

(57) ABSTRACT

A new and distinct *Roscoea* plant characterized by its combination of thick, deep red stems, wide, dark leaves with deep red backs, large purple flowers, and excellent vigor.

1 Drawing Sheet

Botanical denomination: *Roscoea purpurea.*
Variety designation: 'Spice Island'.

BACKGROUND OF THE INVENTION

The present invention relates to a new and distinct *Roscoea purpurea*, and given the cultivar name 'Spice Island'. *Roscoea* is in the family Zingiberaceae. *Roscoea purpurea* 'Spice Island' is a result of a planned breeding cross to make a thick, dark stemmed, dark leaf *Roscoea purpurea*. The parents were proprietary unreleased seedlings using 7-3, as the seed parent, and 5-1, as the pollen parent.

Compared to *Roscoea purpurea* 'Brown Peacock' (an unpatented plant), the other dark leaf *Roscoea* on the market, the new variety has thicker, darker stems and wider leaves. It is also more vigorous.

SUMMARY OF THE INVENTION

The new variety is unique with its combination of thick, deep red stems, wide, dark leaves with deep red backs, large purple flowers, and excellent vigor.

This new cultivar has been reproduced only by asexual propagation (division, tissue culture). Each of the progeny exhibits identical characteristics to the new cultivar. Asexual propagation by tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a 1-year-old plant in of *Roscoea* 'Spice Island' in a one-gallon container in bloom in early June in Canby, Oreg.

DETAILED PLANT DESCRIPTION

The following is a detailed description of the new *Roscoea* cultivar based on observations of 2-year-old plants grown in full shade outside in the trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:
- *Type.*—Rhizomatous herbaceous perennial.
- *Hardiness.*—USDA Zones 6 to 9.
- *Size.*—Grows to 33 cm wide and 34 cm tall from the top of the soil to the top of the plant.
- *Form.*—Clumping.
- *Pseudostems.*—About 6, under the leaf sheaths, grow to 15 cm long and 10 mm wide, glabrous, Yellow Green 149D.

Leaf:
- *Type.*—Simple.
- *Shape.*—Linear lanceolate.
- *Arrangement.*—In two ranks and spirally up the stem.
- *Blade size.*—Grows to 26 cm long and 5 cm wide.
- *Margins.*—Entire and undulate.
- *Apex.*—Acuminate.
- *Base.*—Sheathing.
- *Surface texture.*—Glabrous on both surfaces.
- *Venation.*—Parallel with prominent main vein.
- *Color.*—Topside between Green 139A and Yellow Green 147A bottom side Greyed Purple 187A.

Inflorescence:
- *Type.*—Terminal condensed spikes.
- *Number of flowers per spike.*—About 20 on older stems.
- *Inflorescence.*—17 cm long and 10 cm wide.
- *Peduncle.*—Grows under the upper leaf sheaths.
- *Pedicle description.*—None.
- *Bloom time.*—Late July to early September in Canby, Oreg.
- *Lastingness.*—An inflorescence lasts for 4 to 8 weeks depending on the temperatures.

Flower bud:
- *Size.*—12 cm long and 6 mm wide.
- *Shape.*—Narrow, cylindrical.
- *Surface texture.*—Glabrous.
- *Color.*—Greyed Purple 187A to 187B.

Flower:

*Type*.—Zygomorphic.

*Shape*.—Orchid-like with a tubular corolla and a large showy 2 lobed upper lip.

*Size*.—Grows to 6 cm wide and 21 cm deep.

*Surface texture*.—Glabrous inside and outside.

*Corolla description*.—3 lobed from tube 12 cm long and 3 mm wide, tube Greyed Purple 186B; lower lip large (6 cm long and 3.5 cm wide), reflexed, obovate, with one deep notch, margin entire, tip obtuse, glabrous, topside Purple Violet N82A with White NN155D at base, bottom side N82B; two upper petals form a hood, each 3 cm long and 8 mm wide, irregularly obovate, margin entire, tip acute, glabrous on both sides, both sides N82D with base NN155D.

*Calyx description*.—3 lobed from tube 12 cm long and 3 mm wide, tube Greyed Purple 186B; upper lobe hooded, 53 mm long and 10 mm wide, back side Purple 77A in middle with Greyed Purple 185B on sides, inside closest to Greyed Purple 186C with center White N155C; 2 lower lobes reflexed 45 mm long and 4 mm wide, inside Purple 76A, back side Purple 76B.

*Pistil description*.—17.3 cm long, ovary 2.7 cm long and 5 mm wide and White N155D, style 14.5 cm long, White NN155D, stigma 1 mm long and 1 mm wide, White NN155D.

*Staminodes*.—2, 22 mm long and 1 mm wide, White NN155D, anthers 10 mm long and White NN155A, pollen White NN155A.

*Fragrance*.—None.

Fruit:

*Type*.—3 segmented capsule.

*Size*.—11 mm long, 10 mm wide.

*Shape*.—Broad.

*Color*.—Greyed Purple 187A.

Seed:

*Number*.—0 to 2 per capsule.

*Size*.—3 mm long and 1.5 mm wide.

*Shape*.—Oval.

*Color*.—Black 202A.

Pest and diseases: Pests and diseases are infrequent on *Roscoea* spp. No problems have been observed on this plant grown under commercial conditions in Canby, Oreg.

I claim:

1. A new and distinct *Roscoea* plant as herein shown and described.

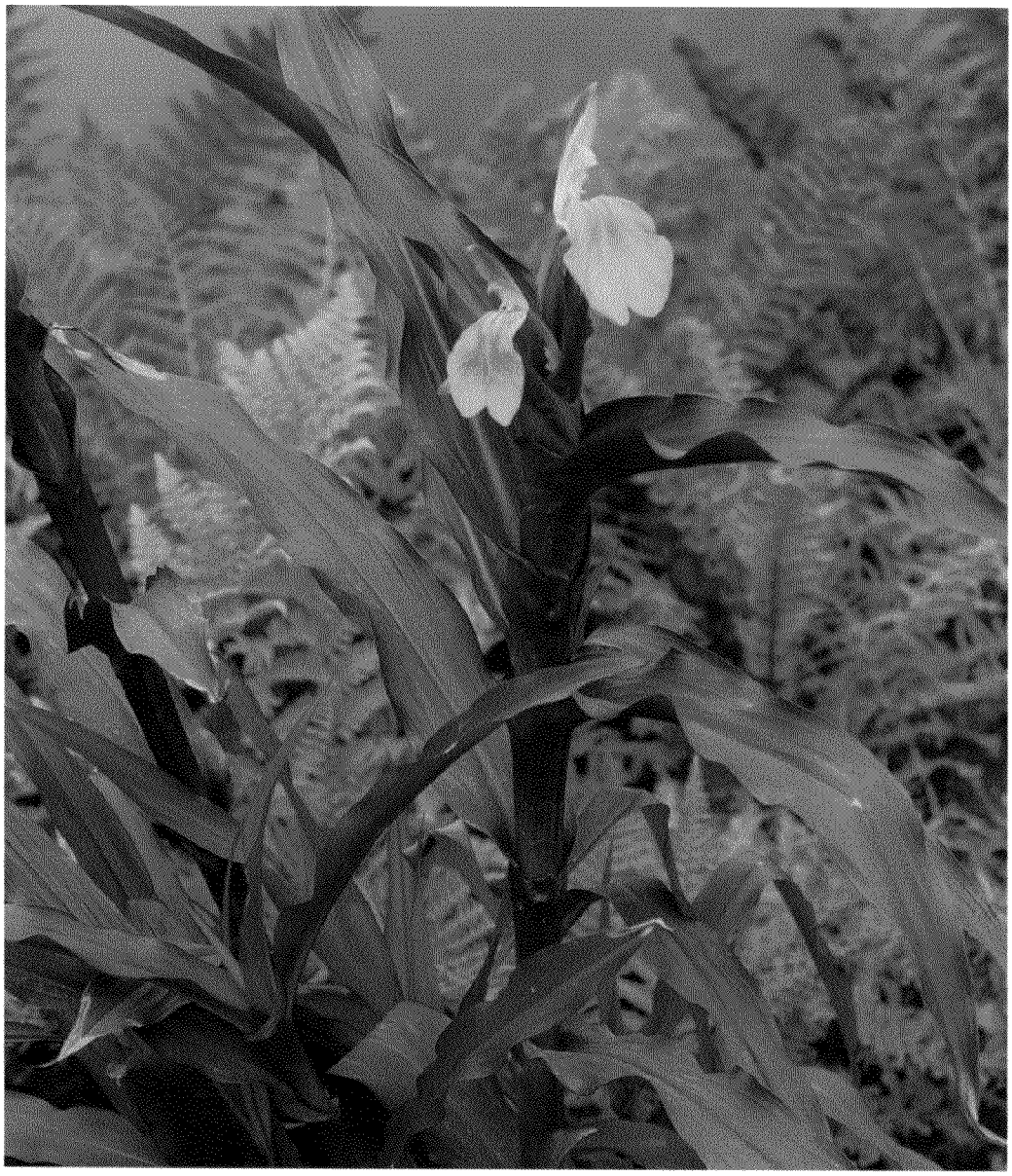

* * * * *